US012751868B2

(12) United States Patent
Subdiaga Rondon et al.

(10) Patent No.: US 12,751,868 B2
(45) Date of Patent: Oct. 6, 2026

(54) ABSORBENT ARTICLE WITH FASTENING COMPONENT FOR DISPOSAL

(71) Applicant: The Procter & Gamble Company, Cincinnati, OH (US)

(72) Inventors: Edisson Reinaldo Subdiaga Rondon, Bad Soden (DE); Petra Ballenberger, Kronberg (DE); JoBeth Martin, Cincinnati, OH (US); Koichi Morimoto, Cincinnati, OH (US); Jason Edward Naylor, Loveland, OH (US); Susanne Osbahr, Idstein (DE); Ekaterina Ponomarenko, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 347 days.

(21) Appl. No.: 18/354,773

(22) Filed: Jul. 19, 2023

(65) Prior Publication Data

US 2024/0033135 A1 Feb. 1, 2024

(30) Foreign Application Priority Data

Jul. 28, 2022 (WO) ................ PCT/CN2022/108528

(51) Int. Cl.
*A61F 13/49* (2006.01)
*A61F 13/84* (2006.01)

(52) U.S. Cl.
CPC . *A61F 13/49011* (2013.01); *A61F 2013/8497* (2013.01)

(58) Field of Classification Search
CPC .......... A61F 13/49011; A61F 13/49061; A61F 13/51478; A61F 13/51498; A61F 13/5512; A61F 13/5655; A61F 2013/8497
See application file for complete search history.

(56) References Cited

U.S. PATENT DOCUMENTS 5,807,371 A * 9/1998 Toyoda .................. A61F 13/56 604/389
2006/0129119 A1 6/2006 Kistler

FOREIGN PATENT DOCUMENTS

JP 2004-329657 * 11/2004 ........... A61F 13/496
WO 2020029240 A1 2/2020

OTHER PUBLICATIONS

PCT Search Report and Written Opinion for PCT/CN2022/108528 dated Jan. 25, 2023; 13 pages.
Extended European Search Report and Search Opinion; Application No. 23186649.2 ; dated Nov. 30, 2023; 09 pages.

* cited by examiner

*Primary Examiner* — Michele Kidwell
(74) *Attorney, Agent, or Firm* — Anna E. Haller; Amanda Herman Berghauer

(57) ABSTRACT

An absorbent article having a fastening component including a plurality of hooks. The fastening component is positioned adjacent to the proximal edge of at least one of the first belt or the second belt of the absorbent article, and the hooks are covered by the wearer-facing surface of the belt. In a wrapped configuration, the fastening component is configured to engage the side panels such that the leg openings are at least partially sealed providing for convenient and hygienic disposal.

20 Claims, 12 Drawing Sheets

ABSORBENT ARTICLE WITH FASTENING COMPONENT FOR DISPOSAL

CROSS REFERENCE TO RELATED APPLICATION

This application claims priority under 35 U.S.C. § 119 to Chinese Patent Application Serial No. PCT/CN2022/108528, filed on Jul. 28, 2022, the entire disclosure of which is hereby incorporated by reference.

FIELD OF THE INVENTION

The present disclosure relates to an absorbent article with a fastening component, and in particular to an absorbent article with a fastening component configured to hold the article in a wrapped configuration to at least partially seal the leg openings for disposal.

BACKGROUND OF THE INVENTION

Infants and other incontinent individuals wear absorbent articles such as diapers or absorbent pants to receive and contain urine and other body fluids such as feces. Absorbent pants may include pull-on absorbent articles, or pant-type absorbent articles, which are donned by inserting the wearer's legs into pre-formed leg openings and sliding the article up into position about the lower torso. After use, absorbent pants are usually folded or rolled into a more compact configuration for disposal using a disposal fastener. However, current disposal fasteners hold used absorbent pants in a configuration that leaves the leg openings unsealed, potentially allowing urine and feces to seep out.

There is a need for an absorbent article to more efficiently prevent bodily exudates from seeping out of a used and soiled absorbent article after removal, including while disposing and once in waste containers. Further, there is a need to provide a convenient and/or more hygienic means for disposing of a soiled absorbent article.

SUMMARY OF THE INVENTION

The present disclosure solves the problems of the undesirable, unhygienic disposal fasteners of absorbent articles by providing one or more fastening components capable of holding the absorbent article in a wrapped configuration such that the leg openings are at least partially sealed and prevent bodily exudates from seeping out during disposal.

An absorbent article comprises a chassis comprising a topsheet, a backsheet, and an absorbent core positioned between the topsheet and the backsheet. The chassis further comprises a first end region and a second end region longitudinally separated from the first end region by a crotch region. The absorbent article also comprises a first belt connected with the first end region of the chassis and a second belt connected with the second end region of the chassis. Laterally opposing side edges of the second belt are connected with laterally opposing side edges of the first belt to form a waist opening and two leg openings. At least one of the first belt and the second belt comprises a distal edge extending along a portion of the waist opening; a proximal edge extending along a portion of each of the leg openings; an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet. The absorbent article also comprises a fastening component. The fastening component comprises a base comprising a first surface, a second surface opposite the first surface, and a plurality of hooks extending from the second surface. The first surface of the base is bonded with the backsheet, and the plurality of hooks are covered by the wearer-facing surface of the inner sheet.

An absorbent article comprises a chassis comprising a topsheet, a backsheet, and an absorbent core positioned between the topsheet and the backsheet. The chassis further comprises a first end region and a second end region longitudinally separated from the first end region by a crotch region. The absorbent article also comprises a first belt connected with the first end region of the chassis; a second belt connected with the second end region of the chassis. Laterally opposing side edges of the second belt are connected with laterally opposing side edges of the first belt to form a waist opening and two leg openings. At least one of the first belt and the second belt comprises a distal edge extending along a portion of the waist opening; a proximal edge extending along a portion of each of the leg openings; an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet. The absorbent article also comprises a fastening component comprising a plurality of hooks. The fastening component is positioned adjacent to the proximal edge of at least one of the first belt and the second belt. The hooks are covered by the wearer-facing surface of the inner sheet.

An absorbent article comprises a chassis comprising a topsheet, a backsheet, and an absorbent core positioned between the topsheet and the backsheet. The chassis further comprises a first end region and a second end region longitudinally separated from the first end region by a crotch region. The absorbent article also comprises a first belt connected with the first end region of the chassis and a second belt connected with the second end region of the chassis. Laterally opposing side edges of the second belt are connected with laterally opposing side edges of the first belt to form a waist opening and two leg openings. At least one of the first belt and the second belt comprises a distal edge extending along a portion of the waist opening; a proximal edge extending along a portion of each of the leg openings; an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet. The absorbent article also comprises two or more fastening components. Each fastening component comprises a base comprising a first surface; a second surface opposite the first surface, and a plurality of hooks extending from second surface. The first surface of the base is bonded with the backsheet and each of the fastening components are covered by the wearer-facing surface of the inner sheet.

An absorbent article comprises a chassis comprising a topsheet, a backsheet, and an absorbent core positioned between the topsheet and the backsheet. The chassis further comprises a first end region and a second end region longitudinally separated from the first end region by a crotch region. The absorbent article also comprises a first belt connected with the first end region of the chassis; a second belt connected with the second end region of the chassis. Laterally opposing side edges of the second belt are connected with laterally opposing side edges of the first belt to form a waist opening and two leg openings. At least one of the first belt and the second belt comprises a distal edge extending along a portion of the waist opening; a proximal edge extending along a portion of each of the leg openings; an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet. The absorbent article also comprises of two or more fastening components, each fastening component comprising of a plurality of hooks, wherein the fastening components are bonded with the backsheet and wherein each of the fastening components are covered by the wearer-facing surface of the inner sheet.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION OF THE INVENTION

Definitions

Figure 1:
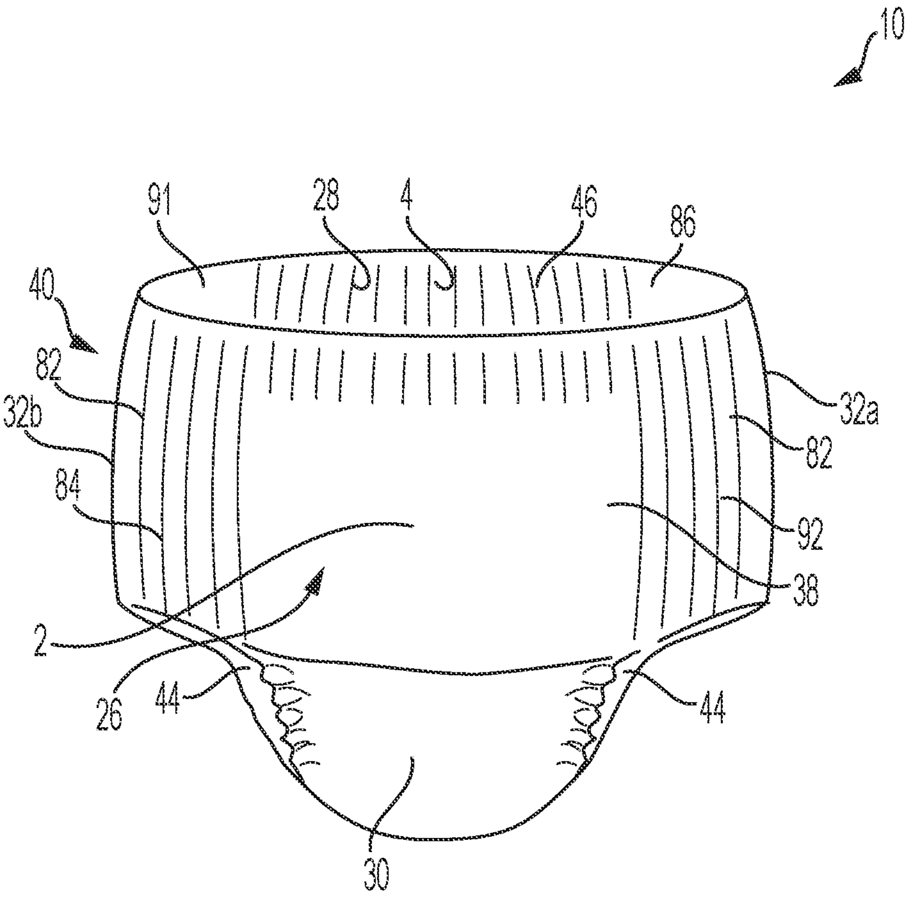
FIG. 1 is a perspective view of an absorbent article, according to one or more configurations shown and described herein.

The following term explanations may be useful in understanding the present disclosure.

As used herein, "absorbent article" refers to devices such as consumer products that absorb and contain body exudates and, more specifically, refers to devices which are placed against or in proximity to the body of the wearer to absorb and contain the various exudates discharged from the body such as soils and wastes. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, sanitary napkins, and the like. Non-limiting examples of absorbent pants include training pants, pull-on or refastenable pant-type diapers, incontinence briefs and undergarments, and the like.

As used herein, "wearer-facing" and "garment-facing" refer respectively to the relative location of an element or a surface of an element or group of elements. "Wearer-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

As used herein, "disposable" refers to absorbent articles which generally are not intended to be laundered or otherwise restored or reused as an absorbent article (e.g., they are intended to be discarded after a single use and may also be configured to be recycled, composted, or otherwise disposed of in an environmentally compatible manner. Some configurations of the absorbent articles described herein are disposable, others maybe reusable or partially reusable.

In regard to structural terms, as used herein, "disposed" means that an element(s) is located in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s), which in turn are affixed to the other element.

As used herein, "integral" means configurations whereby an element is created from or created by an article component, or portions thereof, as opposed to being joined to the component. "Integrally formed" means an element is created from an underlying material or portion thereof, by for example molding, shaping and/or reconstituting the material.

In regard to material terms used herein, the term "nonwoven" refers to a material made from continuous (long) filaments (fibers) and/or discontinuous (short) filaments (fibers) by processes such as spunbonding, meltblowing, carding, and the like. In some configurations, a nonwoven may comprise a polyolefin-based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern.

The present disclosure relates to absorbent articles having disposal mechanisms, and more particularly, to an absorbent article having a fastening component covered by the wearer-facing surface of at least one of the front belt or the back belt which can engage and secure the absorbent article in a compact configuration that at least partially seals the leg openings and waist opening to prevent bodily exudates from seeping out prior to and/or during disposal.

Figure 2:
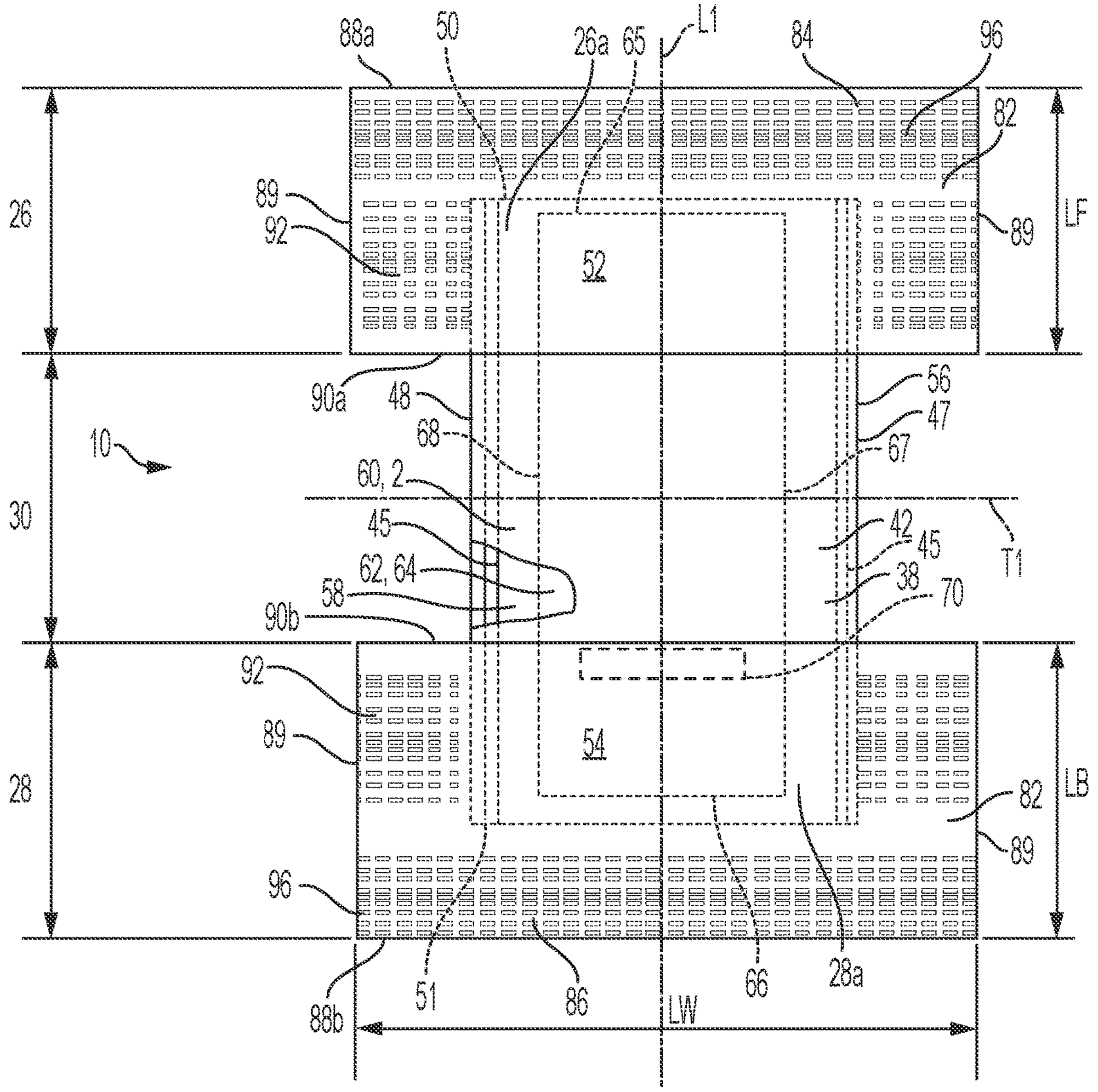
FIG. 2 is a plan view of an absorbent article with the seams unjoined and in a flat uncontracted condition showing the garment-facing surface.

Referring to FIGS. 1-2, an example absorbent article 10 in the form of a diaper pant is illustrated. Although shown in the form of a diaper pant, it is also contemplated that the present disclosure may be used for making a wide variety of diapers, including adult incontinence products, pants, or other absorbent articles, such as sanitary napkins and absorbent pads, for example. FIG. 1 is a front perspective view of an absorbent article 10. FIG. 2 is a plan view of absorbent article with the seams unjoined and in a flat uncontracted condition showing garment-facing surface 2. The absorbent article 10 comprises a wearer-facing surface 4, a garment-facing surface 2, a chassis 38, and a ring-like elastic belt 40 extending transversely defining waist opening 46. As discussed below in more detail, a first belt 84 and a second belt 86 are joined together to form the ring-like elastic belt 40. The absorbent article 10 and the chassis 38 each include a first waist region 26, a second waist region 28, and a crotch region 30 disposed intermediate the first and second waist regions. It may also be described that the chassis 38 includes a first end region 26*a*, a second end region 28*a*, and a crotch region 30 disposed intermediate the first and second end regions 26*a*, 28*a*. The first belt 84 may be connected with the first end region 26*a* of the chassis 38 and the second belt 86 may be connected with the second end region 28*a* of the chassis 38. The first waist region 26 may be configured as a front waist region, and the second waist region 28 may be configured as back waist region.

As shown in FIG. 2, the chassis 38 may include a backsheet 60 and a topsheet 58. The chassis 38 may also include an absorbent assembly 62, including an absorbent core 64, disposed between a portion of the topsheet 58 and the backsheet 60. The periphery of the chassis 38 may be defined by the first longitudinal side edge 47, a second longitudinal side edge 48, a first laterally extending end edge 50 disposed in the first waist region 26, and a second laterally extending end edge 51 disposed in the second waist region 28. Both side edges 47 and 48 extend longitudinally between the first end edge 50 and the second end edge 51.

The vicinity of the first and second longitudinal side edges 47, 48 of the chassis 38 may include and/or may be formed into a pair of elasticized leg cuffs 45 extending transversely outward from the chassis 38. The elasticized leg cuffs 45 may be configured in various ways to help reduce the leakage of body exudates in the leg regions. Example elasticized leg cuffs 45 may include those described in U.S. Pat. Nos. 3,860,003; 4,909,803; 4,695,278; 4,795,454; 4,704,115; 4,909,803; and U.S. Patent Publication No. 2009/0312730 A1, all of which are incorporated by reference herein.

As mentioned above, the chassis 38 may also comprise an absorbent assembly 62. As shown in FIG. 2, the absorbent assembly 62 may have a laterally extending front edge 65 in the first waist region 26 and may have a longitudinally opposing and laterally extending back edge 66 in the second waist region 28. The absorbent assembly 62 may have a longitudinally extending right side edge 67 and may have a laterally opposing and longitudinally extending left side edge 68, both absorbent assembly side edges 67 and 68 may extend longitudinally between the front edge 65 and the back edge 66. The absorbent assembly 62 may additionally include one or more absorbent cores 64 or absorbent core layers. The absorbent core 64 may be at least partially disposed between the topsheet 58 and the backsheet 60 and may be formed in various sizes and shapes that are compatible with the absorbent article. Exemplary absorbent structures for use as the absorbent core of the present disclosure are described in U.S. Pat. Nos. 4,610,678; 4,673,402; 4,888,231; and 4,834,735, all of which are incorporated by reference herein.

Some absorbent core configurations may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,562,646; 5,669,894; and 6,790,798 as well as U.S. Patent Publication Nos. 2004/0158212 A1 and 2004/0097895 A1, all of which are incorporated by reference herein.

As mentioned above, the absorbent article 10 may comprise a topsheet 58. The topsheet 58 may define all or part of the inner, wearer-facing surface of the chassis 38. The topsheet 58 may be liquid pervious, permitting liquids (e.g., menses, urine, and/or runny feces) to penetrate through its thickness. The topsheet 58 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof.

If the topsheet 58 includes fibers, the fibers may be spunbond, carded, wet-laid, meltblown, hydroentangled, or otherwise processed as is known in the art. Topsheets 58 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539. The topsheet 58 may be hydrophilic or hydrophobic or may have hydrophilic and/or hydrophobic portions or layers. If the topsheet 58 is hydrophobic, typically apertures will be present so that bodily exudates may pass through the topsheet 58.

As mentioned above, the absorbent article 10 may comprise a backsheet 60, which may define the outer, garment-facing surface 2 of the chassis 38. In some configurations, the backsheet 60 may be configured to prevent exudates absorbed and contained within the chassis from soiling articles that may contact the absorbent article, such as bedsheets and undergarments. In certain configurations, the backsheet 60 may be substantially water impermeable. The backsheet 60 may, for example, be or comprise a thin plastic film, such as a thermoplastic film having a thickness of about 0.012 mm to about 0.051 mm. Other suitable backsheet materials may include breathable materials that permit vapors to escape from the absorbent article while still preventing exudates from passing through the backsheet 60.

Backsheet 60 may also comprise of more than one layer. For example, the backsheet 60 may comprise an outer cover and an inner layer. The outer cover may be made of a soft, nonwoven material. The inner layer may be made of a substantially liquid-impermeable film, such as a polymeric film. The outer cover and inner layer may be joined together by adhesive or any other suitable material or method. The outer cover material may comprise a bond pattern, apertures, and/or three-dimensional features. The outer cover may be a hydroentangled nonwoven material.

As mentioned above, the absorbent article 10 may comprise a ring-like elastic belt 40. The ring-like elastic belt 40 may be defined by a first belt 84 connected with a second belt 86. The first belt 84 and second belt 86 (sometimes referred to as "first and second belts") may be joined with each other at side edges 89 to form two side seams 32*a*, 32*b* (as shown in FIG. 1). The side seams 32*a*, 32*b* may be any suitable seams, such as butt seams or overlap seams, for example. The side seams 32*a*, 32*b* may be permanently joined using adhesives or bonds, for example, or may be refastenably closed using hook and loop fasteners, for example.

Referring to FIG. 2, the central region of the first belt 84 may be connected with the first waist region 26 or first end region 26*a* of the chassis 38, and the central region of the second belt 86 may be connected with the second waist region 28 or second end region 28*a* of the chassis 38. The first and second belts 84, 86 and the chassis 38 jointly define two leg openings 44. Each leg opening 44 may be provided with elasticity around the perimeter of the leg opening by the combination of elasticity from the first belt 84, the second belt 86, and from the chassis 38. In some configurations, the first belt 84 may be configured as a front belt, and the second belt 86 may be configured as a back belt.

The first belt 84 and second belt 86 are configured to impart elasticity to the ring-like elastic belt 40. The first and second belt 84, 86 each have transversely continuous proximal and distal edges, the proximal edge 90*a*, 90*b* of the first and second belt 84, 86, respectively, being located closer than the distal edge 88*a*, 88*b* of the first and second belt 84, 86, respectively, relative to the transverse center line T1. The first belt 84 and the second belt 86 may each be formed by a laminate comprising an elastic material 96 extending in the transverse direction, an inner sheet 91(shown in FIG. 1), an outer sheet 92, and an outer sheet fold over directly joined to the chassis 38. The outer sheet fold over is an extension of the outer sheet formed by folding the outer sheet material at the distal edge 88*a*, 88*b* of the first and second belts 84, 86. The belt elastic material 96 may extend in the transverse direction to provide a ring-like belt 40 when the first belt 84 and the second belt 86 are joined. At least some of the elastic material 96 may extend in the transverse direction substantially parallel to each other. In some configurations, all of the elastic material 96 may extend in the transverse direction substantially parallel to each other. It is to be appreciated that the elastic material 96 may include one or more elastic elements such as strands, ribbons, elastic films, or panels extending along the lengths of the elastic belts. The elastic material 96 may comprise a plurality of elastic strands. The elastic material 96 may be disposed with the same or different denier, interval, or force between the first and second belts, as well as in different longitudinal positions of the belt. The inner and outer sheets 91, 92 may be the same or different material, and selected to provide characteristics such as breathability, softness, cushiony feel, loftiness, and combinations thereof, depending on the desirables of the resulting article. The inner and outer sheets 91, 92 may have the same or different basis weight, stiffness, texture, or any combination thereof.

Still referring to FIG. 2, the transverse width LW of the second belt 86 in the uncontracted condition may be the same as the transverse width of the first belt 84 of the same condition. The longitudinal length LB of the second belt 86 between the second belt distal edge 88*b* and the second belt proximal edge 90*b* along its entire width LW may be approximately the same as the longitudinal length LF of the first belt 84 between the first belt distal edge 88*a* and the first belt proximal edge 90*a*. In such configuration, the seams close the first and second belt 84, 86 side edges 89 of the same length for forming the article.

The second belt 86 may have a greater longitudinal length LB between the second belt distal edge 88*b* and the second belt proximal edge 90*b* along its entire width LW in the transverse direction than the longitudinal length LF of the first belt 84 between the first belt distal edge 88*a* and the first belt proximal edge 90*a*, and this may be particularly useful for increased buttocks coverage when the second belt 86 has a greater longitudinal length versus the first belt 84 adjacent to or immediately adjacent to the side seams.

The first and/or second belt 84, 86 may be treated such that certain of the area overlapping the first waist panel 52 and/or the second waist 54 of the chassis 38 are removed of elasticity. Removal of elasticity from a certain area of the first and/or second waist panel 52, 54 may be advantageous when the chassis 38 comprises an absorbent assembly 62, in that elasticity in the first and/or second waist panel 52, 54 may cause bunching of the absorbent core 64 or any of the layers in the absorbent assembly 62 and interfere with close fit of the chassis 38 to the wearer. At least a portion of, or at least 10% of, or at least 20% of, or at least 30% of, the elasticity of at least one of, or at least half of, or at least two thirds of, the elastic material 96 may be removed in the region overlapping with the first and second waist panels 52, 54 of the chassis 38. The entire area where the elastic material 96 overlaps with the absorbent assembly 62 may be removed of its elasticity.

The first and second belts 84, 86 may be discontinuous with one another in the crotch region and therefore the outer cover layer 42 may define the garment-facing surface of the absorbent article in the crotch region 30. The outer cover layer 42 may extend only partly in the longitudinal direction of the first waist panel 52 and/or the second waist panel 54 to leave the distal parts of the first waist panel 52 and the second waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the first waist panel 52 and the second waist panel 54 are devoid of the outer cover layer 42, which may help provide relatively more breathability to the overall article.

Figure 3:
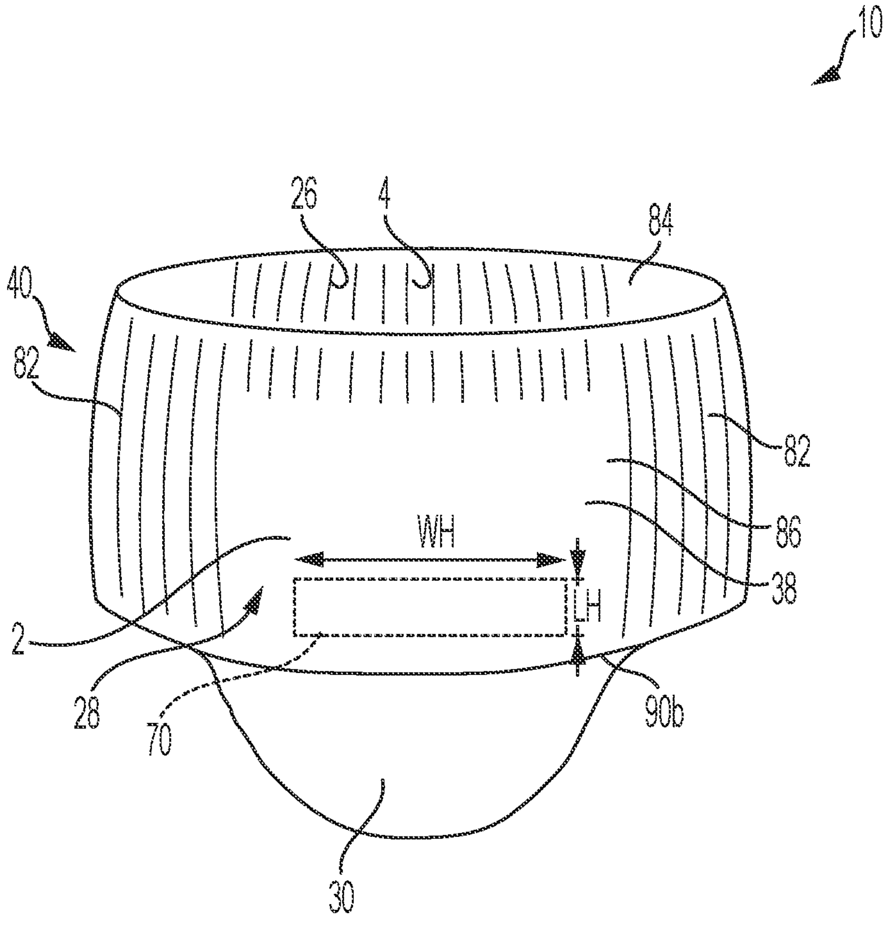
FIG. 3 is a rear perspective view of an absorbent article showing a fastening component covered by the second belt, according to one or more configurations shown and described herein.

As discussed above, the absorbent article 10 may comprise a fastening component 70, such as shown in FIG. 3. The fastening component 70 is configured to engage and hold the absorbent article 10 in a compact configuration that at least partially seals the leg openings and waist opening after use. It is to be appreciated that the fastening component 70 may be configured various ways. For example, the fastening component may include respective components of a hook and-loop fastening system (such as VELCRO®), respective surfaces having a cohesive material applied thereto, male and female snap fastener components, a button and buttonhole, slot or loop, other fastenably cooperating elements, and the like. Other examples of fastening components may include zipper components, "zip lock" engaging components, loops, posts, pockets, bands or straps, microfasteners, macrofasteners, and fastening components such as described in U.S. Pat. Nos. 6,936,039; 6,893,388; 6,669,618; 6,432,098; and 6,251,097, and U.S. Published Applications, Pub. Nos. 2005/0234419; 2005/0215971; 2005/0215970; 2005/0130821; 2004/0023771; 2003/0233082; 2003/0119641; 2003/0088220; and 2002/0169431. In some aspects, the fastening component 70 may comprise hooks or adhesive adapted to refastenably connect with another surface of the absorbent article 10.

It should be appreciated that the fastening component 70 may be any suitable shape and size. For example, the fastening component 70 may be square, rectangular, circular, oval, heart shaped, semi-circular, triangular, or any other suitable shape. The fastening component 70 may have a longitudinal length LH of from about 5 mm to about 50 mm, or from about 10 mm to about mm, or from about 12 mm to about 35 mm. In some configurations, the fastening component has a longitudinal length LH of about 13 mm. The fastening component 70 may have a transverse width WH of from about 20 mm to about 120 mm, or from about 25 mm to about 100 mm, or from about 30 mm to about 90 mm. In some configurations, the fastening component 70 has a transverse width WH of about 80 mm. The fastening component 70 may comprise a two-dimensional area that is at least about 1 $cm^2$, or at least about 3 $cm^2$, or at least about 5 $cm^2$, or from about 1 $cm^2$ to about 60 $cm^2$, or from about 3 $cm^2$ to about 40 $cm^2$, or from about 5 $cm^2$ to about 35 $cm^2$, reciting for each range every 1 $cm^2$ increment therein.

Figure 4:
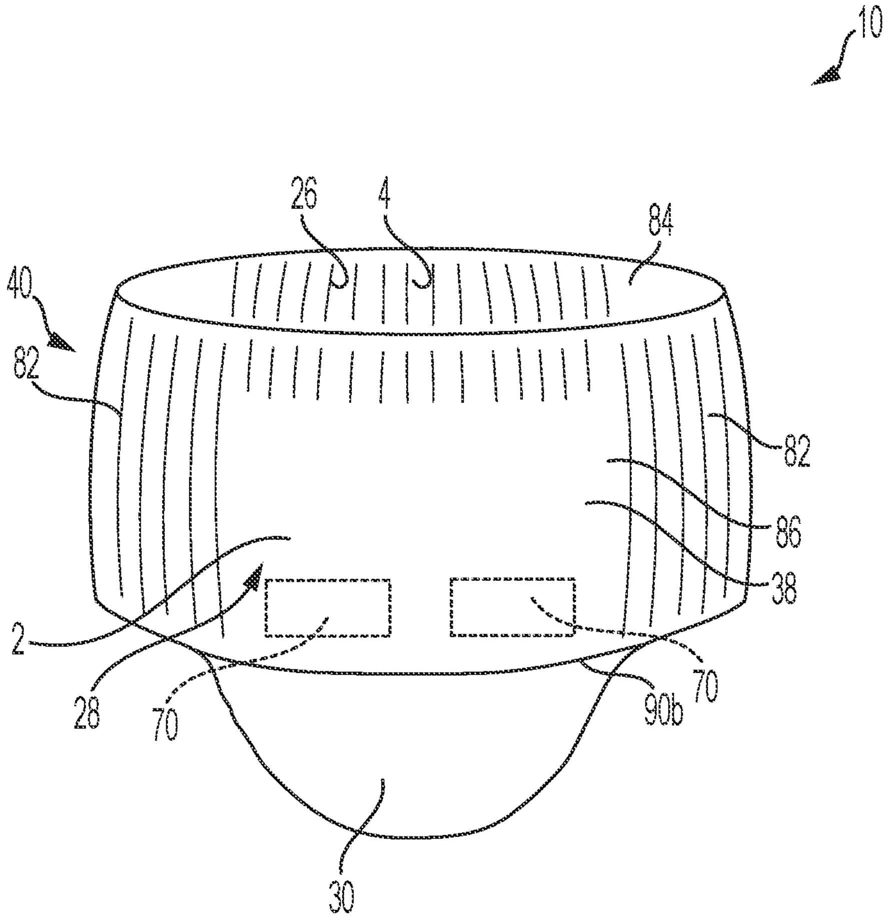
FIG. 4 is a rear perspective view of an absorbent article showing multiple fastening components covered by the second belt, according to one or more configurations shown and described herein.

The absorbent article 10 may comprise more than one fastening component 70, such as, a pair of fastening components as shown, for example, in FIG. 4. In some configurations, the absorbent article 10 may comprise three fastening components, or four or more fastening components. The fastening component 70 may be positioned anywhere on the chassis 38. While FIGS. 3 and 4 show fastening component 70 positioned in the second region 28, it is to be appreciated that the fastening component(s) 70 may also be positioned in any suitable location on the absorbent article, including first region 26 or crotch region 30.

Figure 5:
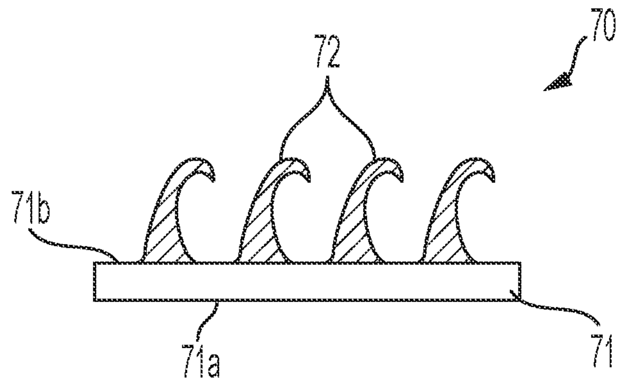
FIG. 5 is a cross-sectional view taken within a fastening component, according to one or more configurations shown and described herein.

As shown in FIG. 5, the fastening component 70 may comprise a base 71 having a first surface 71*a* and a second surface 71*b* opposite the first surface 71*a*, with a plurality of hooks 72 extending outwardly from the second surface 71*b*. The first surface 71*a* may be bonded to the absorbent article. The plurality of hooks 72 may be any shape, such as nub, mushroom, "J" shape, "T" shape, hook shape, or any other shape known in the art, so long as the hooks can refastenably engage with substrates, such as nonwovens for example, on an exterior surface of the absorbent article.

In some aspects, fastening component materials may include molded or extruded nylon, polyester, polypropylene, or other suitable material. In some aspects, the fastening component material may be made by casting, molding, profile extrusion, or microreplication. The fastening component material may be made by using processes described in U.S. Pat. Nos. 3,192,289; 3,138,841; 3,266,113; 3,408,705; 3,557,413; 3,594,863; 3,594,865; 3,718,725; 3,762,000; 4,001,366; 4,056,593; 4,189,809; 4,290,174; 4,454,183; 4,894,060; 5,077,870; 5,315,740; 5,679,302; 5,879,604; 5,845,375; 6,054,091; 6,206,679; 6,209,177; 6,248,419; 6,357,088; 6,481,063; 6,484,371; 6,526,633; 6,635,212; 6,660,202; 6,228,298; 6,737,147; 6,869,554; RE38,652; 6,982,055; 7,014,906; 7,048,818; 7,032,278; 7,052,636; 7,052,638; 7,067,185; 7,172,008; 7,182,992; 7,185,401; 7,188,396; and 7,516,524, each of which is hereby incorporated by reference. Suitable examples of fastening component materials may include commercially available hook material from Aplix, sold under the product codes 963, 745, or 740, and from 3M, sold under the product codes CS200, CS300, or CS600. Depending on the engaging substrate, the hook type may be changed to better suit engagement. Still other hook materials are described in U.S. Pat. No. 5,058,247, which is hereby incorporated by reference.

The base 71 may comprise a base material comprising a woven material, a nonwoven material, a plastic material, a polymeric film such as thermoplastic film of polyethylene or polypropylene, nylon, or composite materials such as a film coated nonwoven material or a film-nonwoven laminate, an adhesive, and combinations thereof. The base may be a laminate of a nonwoven bonded, such as by extrusion bonding or by any other method of bonding including, but not limited to, thermal, adhesive, ultrasonic, or mechanical bonding, to a plastic material comprising a plurality of hooks. In some aspects, the plurality of hooks 72 may be extrusion bonded such as disclosed in, for example, U.S. Patent Publication No. US2021/0045931 A1, which is incorporated herein by reference. In some aspects, the plurality of hooks 72 may be integrally formed directly from a substrate such as base 71 as disclosed in, for example, U.S. Pat. No. 8,784,722 and U.S. Patent Publication Nos. US 2021/0077307 A1; US 2022/0106713 A1; and US 2022/0106714 A1, all of which are incorporated herein by reference. The fastening component 70 may be formed integrally from the backsheet, the first or second belts, which may be in the form of a nonwoven, or a substrate patch, which may be in the form of a woven, nonwoven, a plastic, a film, and combinations thereof, wherein the substrate patch is bonded with the backsheet.

Figure 6:
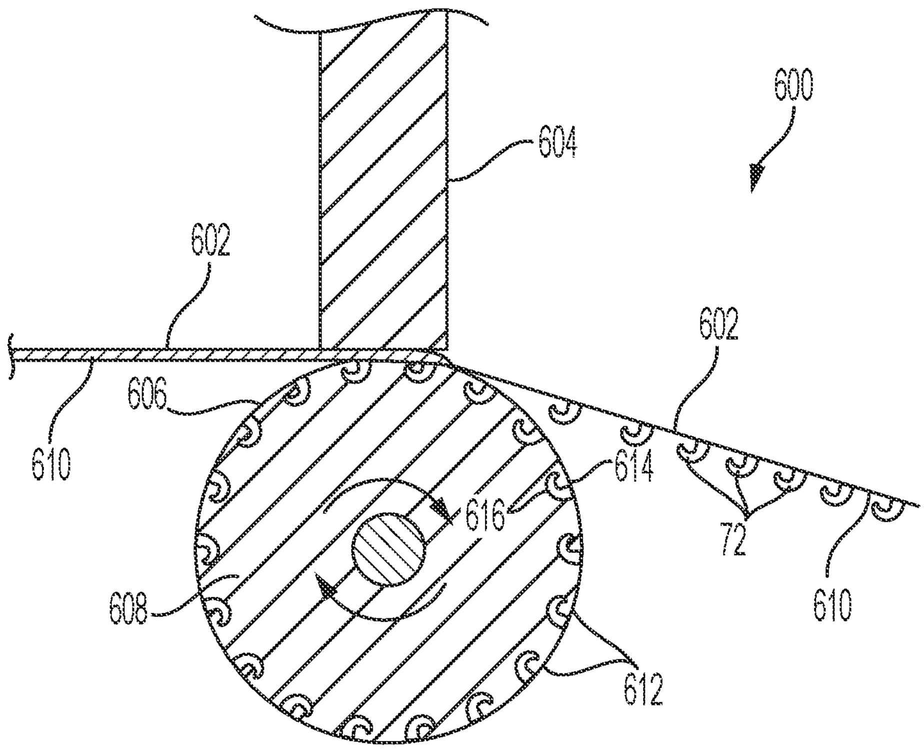
FIG. 6 is a cross-sectional side view of a system for forming hooks that are integral with a substrate, such as a nonwoven or a film.

FIG. 6 is a cross sectional view of a system 600 for forming hooks 72 that are integral with a substrate 602, such as a nonwoven or a film, for example. As shown, the substrate 602 is disposed between a sonotrode 604 and a proximal surface 606 of a tool 608 such that a first side 610 of the substrate contacts the proximal surface of the tool 608. The tool 608 defines a plurality of cavities 612, each of the cavities 612 extending from a base 614 at the proximal surface to a distal end 616 within the tool to define a negative mold of a hook fastener. By way of example, FIG. 6 depicts the tool 608 as a rotating anvil, whereas other embodiments can include a tool with any of various shapes or configurations. The sonotrode 604 is configured to vibrate, for example at one or more ultrasonic frequencies, to locally heat the substrate 602 to cause the substrate to flow into the cavities. Thus, once the substrate is disposed between the sonotrode and the tool, ultrasonic energy is delivered from the sonotrode to the substrate such that a temperature of the first side of the substrate increases above the substrate's glass transition temperature. Thereafter or simultaneously, the substrate may be compressed between the sonotrode and the tool such that the substrate flows into the cavities until the substrate substantially fills the cavities to form a plurality of hooks 72 on first side 610 of the substrate that are integral with the substrate. These hooks may take on a number of geometries based on the shape of the cavities.

While integrating hooks into a substrate, such as a belt laminate, provides some advantages for the product, it also creates some unique technical challenges. First, the amount of nonwoven basis weight required to form hooks ultrasonically may be higher than the basis weight of the belt or backsheet nonwoven typically used for the production of absorbent articles. In order to provide an adequate amount of polymer to form hooks, a local basis weight of at least about 40 gsm to about 80 gsm or higher may be required. Second, the processing speed of a hook forming process as described above may be substantially slower than the web speed applied in typical absorbent article production lines.

To address the challenge of low nonwoven basis weight, a discrete substrate patch comprising a nonwoven may be placed and attached to the belt or backsheet nonwoven in the area where hooks will be formed. Alternatively, a polymer, such as for example Licocene®, may be coated locally onto the belt or backsheet nonwoven in the area where the hooks will be formed. In some aspects, the edge of the belt nonwoven may be folded on top of itself to create a zone of higher basis weight. Once the area of the belt or backsheet nonwoven that is targeted for the hook formation has sufficient basis weight, the hook formation may start.

To address the challenge of slower processing speed, a method of altering the speed of the belt or backsheet web may be deployed. In some aspects, a Festooning apparatus—such as described in U.S. Pat. No. 8,377,249—may be used to cyclically alter the speed of the belt or backsheet nonwoven as the web is fed through the ultrasonic forming apparatus. The speed profile of the web may be adjusted as the web passes through the forming station in a way that the effective speed during the intermittent hook forming process is slower than the average of the web speed, while the web speed during the time when no hook is formed would be higher than average. This would enable production of a laminate with intermittent hooks at a throughput rate higher than the processing speed of the hook forming process itself.

In some aspects, hooks may be formed in a high basis weight nonwoven web at slower speed, then this hook bearing web may be cut into patches, spaced apart and attached as a discrete piece to a nonwoven belt laminate or backsheet.

In some aspects, the processes for hook formation described above may be substituted by processes to attach pre-made or offline formed hooks to the belt or backsheet.

In addition to hooks or instead of hooks, the fastening component 70 may be an adhesive patch comprising a pressure sensitive adhesive or hot melt adhesive. The basis weight of the adhesive may vary from about 10 gsm to about 100 gsm. Non-limiting types of adhesive types may include styrenic block copolymer, polyolefin, polyurethane, acrylic, and combinations thereof.

In some aspects, the fastening component 70 may comprise from about 1000 to about 3000 hooks per square inch, as seen under high resolution image, or from about 1250 to about 2500 hooks per square inch.

In some aspects, the fastening component 70 may comprise hooks having a height (as measured from the second surface 71*b* of the base 71 to the top of the hook head) from between about 120 μm to about 520 μm, as seen under high resolution image, or from about 150 μm to about 400 μm.

In some aspects, the fastening component 70 may comprise hooks having a basis weight (without adhesive) of from about 40 gsm to about 150 gsm.

It is to be appreciated that the fastening component 70 may be joined to the chassis or other absorbent article component in various ways, such as for example with mechanical bonds, thermal bonds, ultrasonic bonds, and/or adhesive bonds. In some configurations, the fastening component may be joined to the backsheet. The fastening component 70 may be joined to the backsheet film or the backsheet nonwoven material. In some aspects, the fastening component 70 may be partially joined to the backsheet film and partially bonded to the backsheet nonwoven material. In some configurations, the fastening component 70 may be joined to the first belt 84 or second belt 86.

Figure 7A:
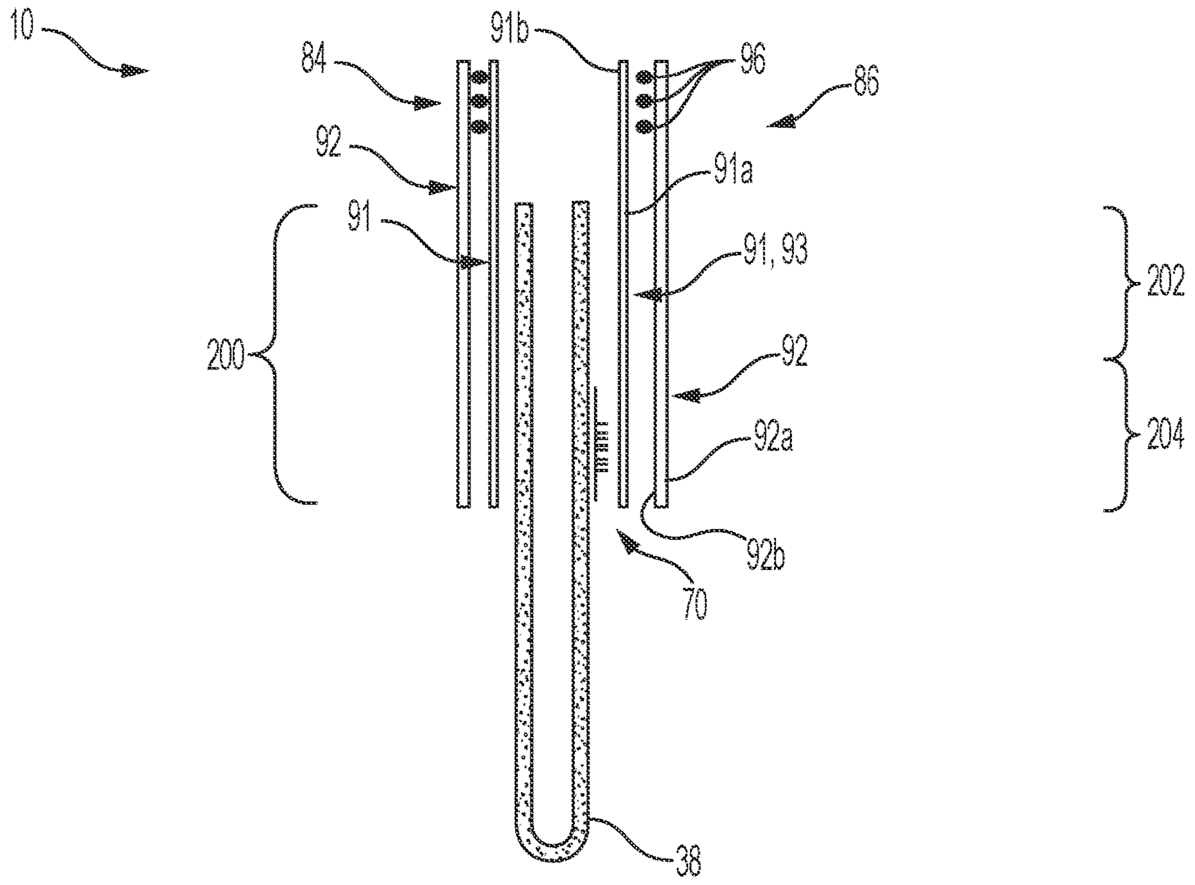
FIG. 7A is a cross-sectional view of the absorbent article showing a fastening component covered by the second belt, according to one or more configurations shown and described herein.
Figure 7B:
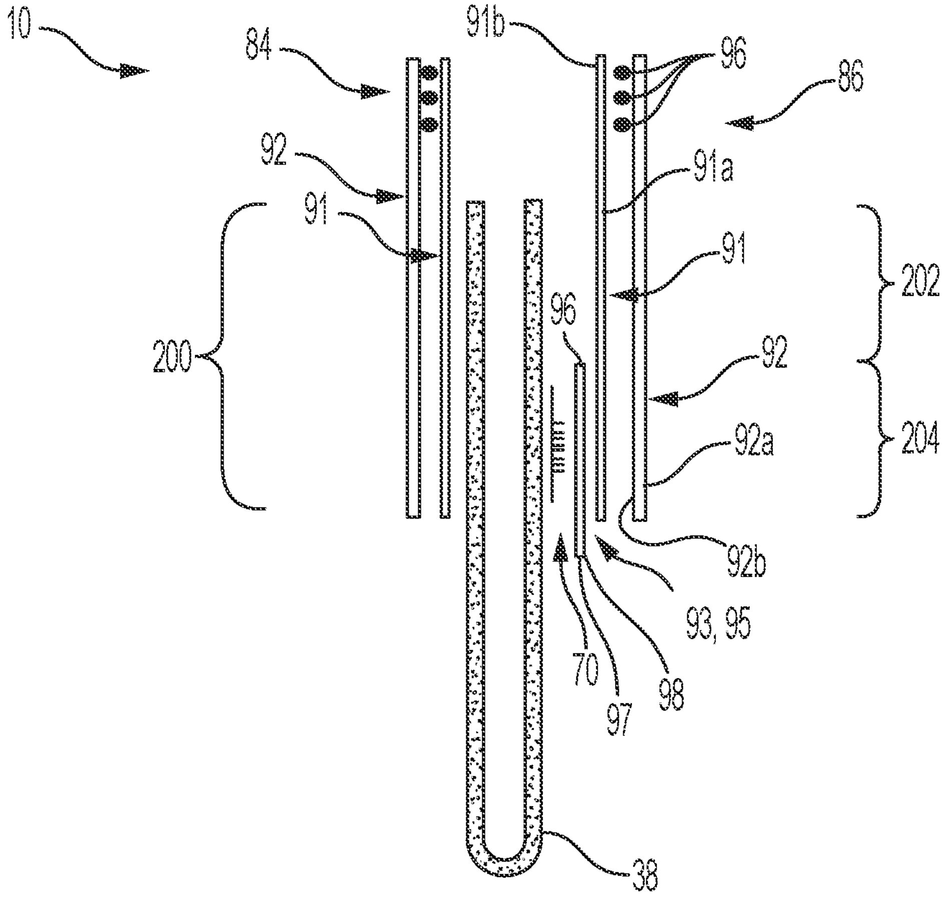
FIG. 7B is a cross-sectional view of the absorbent article showing a fastening component covered by an intermediate layer and the second belt, according to one or more configurations shown and described herein.
Figure 7C:
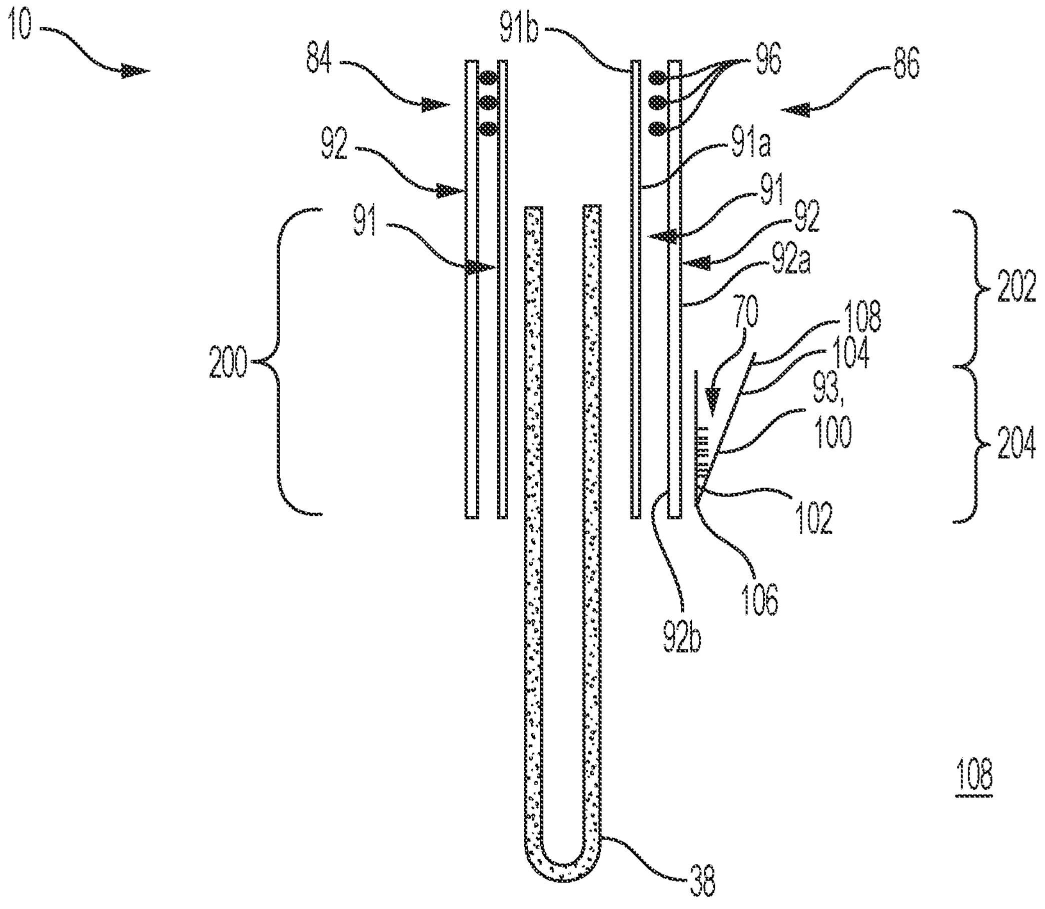
FIG. 7C is a cross-sectional view of the absorbent article showing a fastening component on the second belt and covered by a nonwoven cover, according to one or more configurations shown and described herein.

As previously mentioned, first belt 84 and the second belt 86 may comprise an inner sheet 91 and an outer sheet 92, shown for example in FIG. 7A-7C. The inner sheet 91 may be oriented to define at least a portion of the garment-facing surfaces of the first belt 84 and the second belt 86, and the outer sheet 92 may be oriented to define at least a portion of the wearer-facing surfaces of the first belt 84 and the second belt 86.

The first and/or second belts 84, 86 may include an inner sheet 91, and/or outer sheet 92 that may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some configurations, the first and/or second belts may include an inner sheet 91 and/or outer sheet 92 comprising a nonwoven web of synthetic fibers and may include a stretchable nonwoven. In some configurations, the first and second elastic belts may include an inner hydrophobic, non-stretchable nonwoven material and an outer hydrophobic, non-stretchable nonwoven material. It is to be appreciated that the belts may configured in various ways, such as disclosed for example, in U.S. Patent Application No. 63/111,790 and Chinese Patent Application No. CN2021/077843, which are both incorporated by reference.

As shown in FIG. 7A-7C, the inner sheet 91 may include a garment-facing surface 91*a* and an opposing wearer-facing surface 91*b*, and the outer sheet 92 may include a garment-facing surface 92*a* and an opposing wearer-facing surface 92*b*. The first and second belts 84, 86 may also comprise elastic material 96 positioned between and connected with the garment-facing surface 91*a* of the inner sheet 91 and the wearer-facing surface 92*b* of the outer sheet 92. The first belt 84 and/or the second belt 86 may comprise an overlapping chassis area 200. The overlapping chassis area 200 comprises a first region 202 that is bonded to the chassis 38 and a second region 204 that is not bonded with the chassis 38. Fastening component 70 may be positioned in the second region 204.

At least a portion of, or all of, the fastening component 70 may be covered by a material layer 93 so as to keep the fastening component 70 hidden before the article is ready for disposal. This may help to reduce the risk of the fastening component 70 undesirably catching on clothing or bedsheets while the absorbent article is being worn and makes it more difficult for infants to find and engage with the fastening component 70 while wearing the absorbent article. The fastening component 70 may be configured to refastenably engage the wearer-facing surface of the material layer 93.

In some aspects, the material layer 93 may be the inner layer 91 of first or second belt 84, 86. As shown in FIG. 7A, fastening component 70 may be disposed on chassis 38 under second belt 86 and may be in direct contact with the wearer-facing surface 91*b* of inner sheet 91. Fastening component 70 may be configured to refastenably engage the wearer-facing surface 91*b* of the inner sheet 91. It is to be appreciated that fastening component 70 may also be disposed on chassis 38 under first belt 84.

As shown in FIG. 7B, the material layer 93 may be an intermediate layer 95. The intermediate layer 95 may be joined to the wearer-facing surface 91*b* of inner sheet 91. Fastening component 70 may be in direct contact with the wearer-facing surface of the intermediate layer 95 and may be configured to refastenably engage the wearer-facing surface of intermediate layer 95. In some aspects, an adhesive may be applied to the wearer-facing surface 91*b* of inner sheet 91 during manufacturing to at least partially join inner sheet 91 to the backsheet. By positioning intermediate layer 95 between fastening component 70 and the wearer-facing surface 91*b* of inner sheet 91, interference between the adhesive and the fastening component 70 may be reduced. Intermediate layer 95 may comprise a first end region 96 and a second end region 97. The intermediate layer 95 may also comprise a grip tab 98 at the proximal end of the second end region 97. Grip tab 98 may extend longitudinally past the proximal edge of second belt 86 and may be used by the caregiver to assist in lifting second belt 86 to expose the underlying fastening component 70 for use in disposal. It is to be appreciated that intermediate layer 95 and fastening component 70 may also be disposed under first belt 84. Intermediate layer 95 may comprise a woven material, a nonwoven material, a plastic material, and combinations thereof.

As shown in FIG. 7C, the material layer 93 may be a nonwoven cover 100. In this configuration, the fastening component 70 may disposed on the garment-facing surface 92*a* of outer layer 92 and at least a portion of, or all of, fastening component 70 may be covered by the nonwoven cover 100. Nonwoven cover 100 may be attached to the garment-facing surface 92*a* of outer layer 92. Fastening component 70 may be attached to or form an integral part of nonwoven cover 100. Nonwoven cover 100 may comprise an attachment portion 102 and a cover portion 104, wherein the attachment portion 102 and the cover portion 104 are divided by a fold 106. The attachment portion 102 may be attached to the garment-facing surface 92*a* and the cover portion 104 may be refastenably engaged with the fastening component, holding the nonwoven cover 100 in a folded state. The distal end of cover portion 104 may comprise a grasping portion 108 extending longitudinally past the proximal edge of second belt 86. Grasping portion 108 may serve as a means for the caregiver to release the cover portion 104 from the fastening component 70.

While FIG. 7C shows fastening component 70 disposed on second belt 86, it is to be appreciated that fastening component 70 and nonwoven cover 100 may also be disposed on first belt 84.

The fastening component 70 may be located anywhere along the length of the proximal edge 90*a*, 90*b* of the first belt 84 or the second belt 86. For instance, as illustrated in FIG. 3, the fastening component 70 may be centrally located along the proximal edge 90*b* of the second belt 86. The fastening component 70 may be positioned adjacent to the proximal edge 90*a*, 90*b* of the first belt 84 or the second belt 86. The fastening component 70 may be positioned from about 2 mm to about 15 mm from the proximal edge of the first or second belt 84, 86, or from about 3 mm to about 10 mm, or from about 4 mm to about 8 mm. If the fastening component is too close to the proximal edge, a caregiver may have difficulty gripping and lifting the belt to expose the fastening component for use during disposal. If the fastening component is too far from the proximal edge, a caregiver may have difficulty finding the fastening component when it is positioned under the belt.

The fastening component 70 may include one or more design elements adapted to indicate the location or function of the fastening component including at least one of insignia, letters, words, graphics, logos, colors, fonts, shapes, or combinations thereof. In some configurations, the fastening component 70 may have a color that is visible through any layers of the first or second belts 84, 86 or material layer under which the fastening component 70 is located. In some configurations, the color of the fastening component 70 is different from the color of the surrounding area such that the caregiver can easily identify the location of the fastening component 70. The first and second belt 84, 86 and/or chassis 38 may include printing or other indicia highlighting to a caregiver the location, function, and/or usage of the fastening component 70.

Figure 8A:
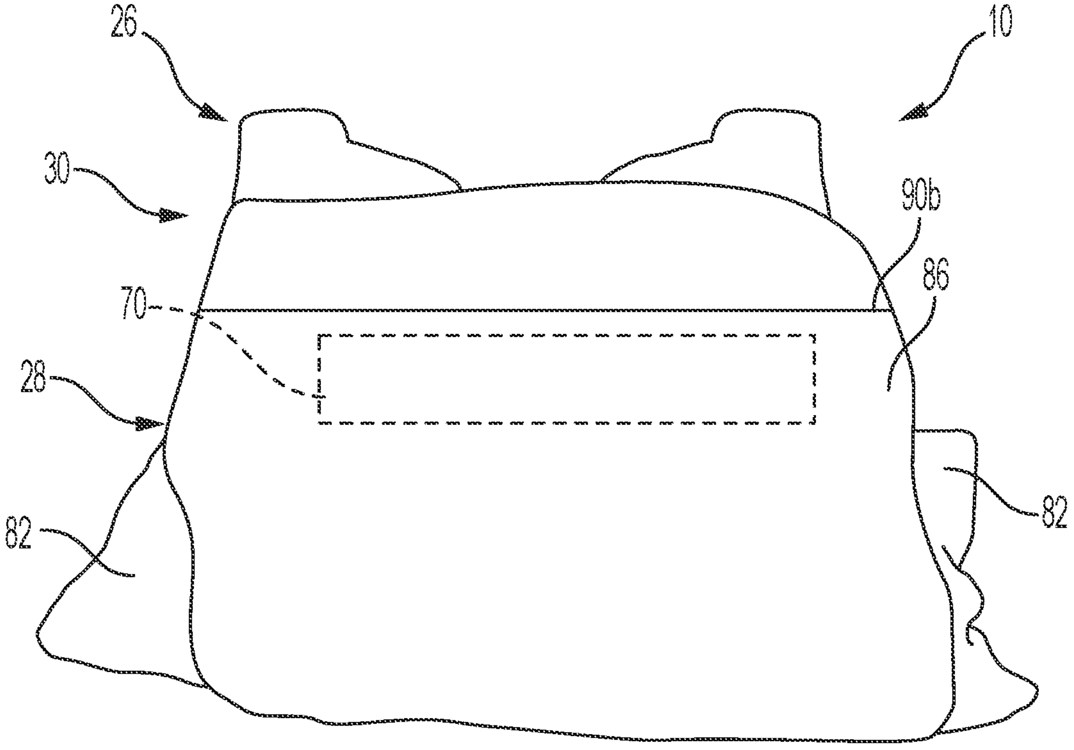
FIG. 8A is a plan view of an example absorbent article comprising a fastening component in a first position in which the crotch and a portion of the second region is folded or rolled up over the first region, according to one or more configurations shown and described herein.
Figure 8B:
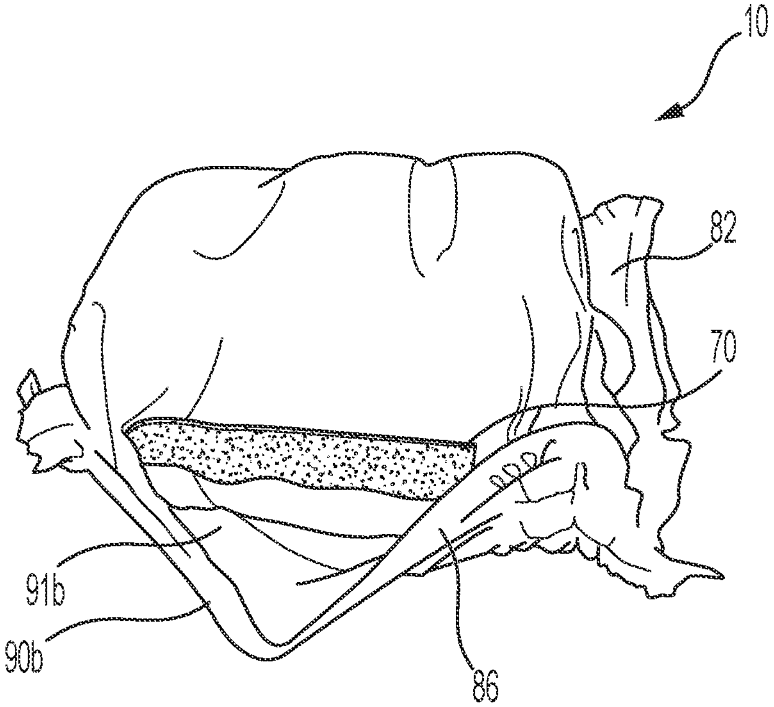
FIG. 8B illustrates the absorbent article of FIG. 8A in a second position in which the second belt has been pulled back to uncover the fastening component.
Figure 8C:
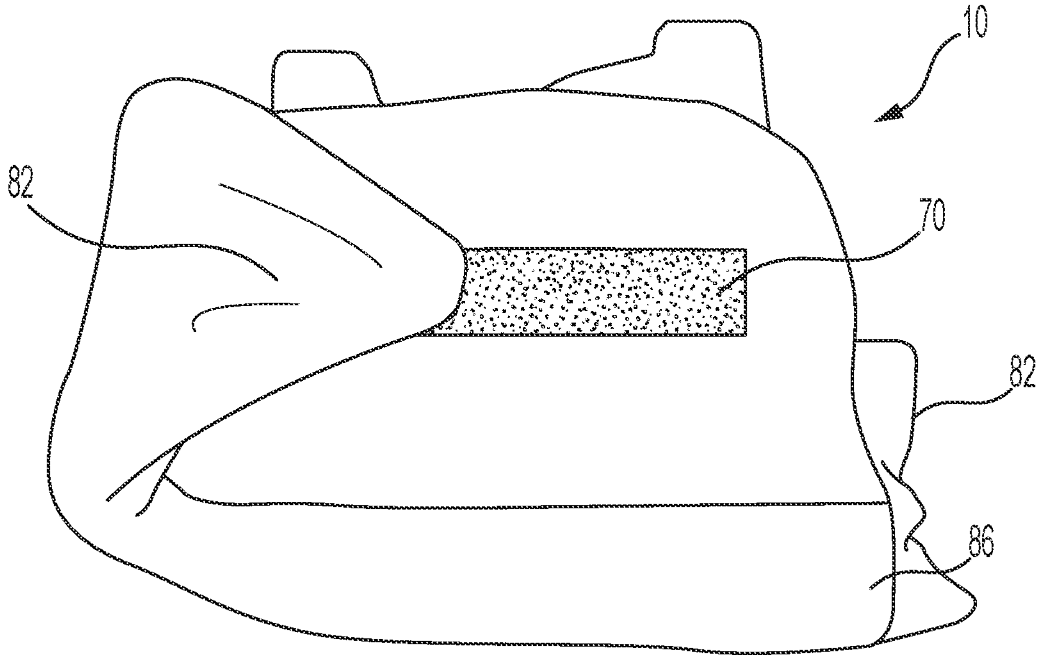
FIG. 8C illustrates the absorbent article of FIG. 8A in a third position in which the side panel is laterally folded inward to engage with the fastening component and to cover an associated leg opening.

FIGS. 8A-8C illustrate the disposal of an exemplary absorbent article 10 comprising a fastening component 70 positioned under the second belt 86. In such a configuration, the fastening component 70 is in direct contact with the wearer-facing surface of the inner sheet and is configured to refastenably engage the wearer-facing surface of the inner sheet. Referring to FIG. 8A, to dispose of the used absorbent article 10 after removal, the crotch region 30 and a portion of the second region 28 may be folded or rolled up over the first region 26. Referring to FIG. 8B, the proximal edge 90*b* of the second belt 86 may then be released from the fastening component 70, such as by peeling back, to expose the underlying plurality of hooks or adhesive for engagement. Referring to FIG. 8C, one or both side panels 82 can then be wrapped in a transverse direction around the absorbent article 10 to engage with the fastening component 70, at least partially sealing the leg opening(s) and sealing, or at least partially sealing, the waist opening to provide convenient and hygienic disposal.

A process for manufacturing the absorbent article 10 may comprise disposing one or more fastening components 70 on the garment-facing surface of a first waist region or second waist region and covering the one or more fastening components 70 with a material layer, such as a belt.

Combinations

A. An absorbent article comprising: a chassis comprising a topsheet, a backsheet, and an absorbent core positioned between the topsheet and the backsheet, the chassis further comprising a first end region and a second end region longitudinally separated from the first end region by a crotch region; a first belt connected with the first end region of the chassis; a second belt connected with the second end region of the chassis, wherein laterally opposing side edges of the second belt are connected with laterally opposing side edges of the first belt to form a waist opening and two leg openings; wherein at least one of the first belt and the second belt comprises: a distal edge extending along a portion of the waist opening; a proximal edge extending along a portion of each of the leg openings; an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet; and a fastening component comprising a plurality of hooks, wherein the fastening component is positioned adjacent to the proximal edge of at least one of the first belt and the second belt, and wherein the plurality of hooks are covered by the wearer-facing surface of the inner sheet.

B. The absorbent article according to paragraph A, wherein the plurality of hooks are in direct contact with the wearer-facing surface of the inner sheet.

C. The absorbent article according to paragraphs A or B, wherein the plurality of hooks are configured to refastenably engage the wearer-facing surface of the inner sheet.

D. The absorbent article according to any of paragraphs A-C, wherein the fastening component comprises a base comprising a first surface, a second surface opposite the first surface, and the plurality of hooks extend from the second surface, wherein the first surface of the base is bonded with the backsheet.

E. The absorbent article according to paragraph D, wherein the base comprises a base material selected from the group consisting of a woven material, a nonwoven material, a plastic material, a polymeric film, a nylon, a composite material, an adhesive, and combinations thereof.

F. The absorbent article according to paragraph E, wherein the plurality of hooks are extrusion bonded with the base material.

G. The absorbent article according to any of paragraphs A-C, wherein the plurality of hooks are integrally formed from the backsheet or a substrate patch bonded with the backsheet.

H. The absorbent article according to any of paragraphs A-G, wherein the laterally opposing side edges of the second belt are refastenably connected with laterally opposing side edges of the first belt.

I. The absorbent article according to any of paragraphs A-H, wherein the absorbent article comprises a first waist region, a second waist region, and a crotch region positioned intermediate the first waist region and the second waist region, wherein the fastening component is positioned in the second waist region.

J. The absorbent article according to any of paragraphs A-I, wherein the fastening component has a transverse width (WH) of from about 20 mm to about 120 mm, preferably from about 25 mm to about 100 mm, more preferably from about 30 mm to about 90 mm.

K. The absorbent article according to any of paragraphs A-J, wherein the fastening component has a longitudinal length (LH) of from about 5 to about 50 mm, preferably from about 10 mm to about 40 mm, more preferably from about 12 mm to about 35 mm.

L. The absorbent article according to any of paragraphs A-K, wherein the absorbent article comprises two or more fastening components.

M. The absorbent article according to any of paragraphs A-L, wherein the absorbent article comprises a garment-facing surface and a wearer-facing surface, wherein the fastening component is visible from the garment-facing surface.

N. The absorbent article according to any of paragraphs A-M, wherein the fastening component is positioned adjacent to the proximal edge of the second belt.

O. The absorbent article according to any of paragraphs A-N, wherein at least one of the first belt, second belt, or backsheet comprises one or more design elements adapted to indicate the location or function of the fastening component, the one or more design elements comprising at least one of insignia, letters, words, graphics, logos, colors, fonts, shapes, or combinations thereof.

P. A method for assembling the absorbent article according to any of paragraphs A-E and H-O comprising the steps of laminating the chassis; laminating the belt; increasing the basis weight of the backsheet nonwoven locally; forming a hook in the area of locally increased basis weight; and cutting, turning and connecting the chassis to the belt.

Q. The method according to paragraph P, wherein the increase of basis weight is achieved by cutting and attaching a substrate patch comprising a nonwoven onto the backsheet.

R. The method according to paragraph P, wherein the increase of nonwoven basis weight is achieved by coating a polymer locally onto the backsheet.

T. The method according to paragraph P, wherein multiple hooks or multiple areas containing hooks are formed.

U. A method for assembling an absorbent article according to any of paragraphs A-E and H-O comprising the steps of laminating the chassis; laminating the belt; providing a substrate patch comprising a nonwoven web having a basis weight of at least 40 gsm; forming a hook in the nonwoven web; cutting the nonwoven web to form a hook patch; spacing the hook patch in the machine direction; attaching the hook patch to the backsheet; and cutting, turning and connecting the chassis to the belt.

V. The method according to paragraph U, wherein the hook patch comprises a plurality of hooks.

W. The method according to paragraph U, wherein the hook is formed ultrasonically.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a chassis comprising a topsheet, a backsheet, and an absorbent core positioned between the topsheet and the backsheet, the chassis further comprising a first end region and a second end region longitudinally separated from the first end region by a crotch region;

a first belt connected with the first end region of the chassis;

a second belt connected with the second end region of the chassis, wherein laterally opposing side edges of the second belt are connected with laterally opposing side edges of the first belt to form a waist opening and two leg openings;

wherein at least one of the first belt and the second belt comprises:

a distal edge extending along a portion of the waist opening;

a proximal edge extending along a portion of each of the leg openings;

an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet; and a fastening component comprising a plurality of hooks, wherein the plurality of hooks are covered by the wearer-facing surface of the inner sheet, wherein the plurality of hooks are in direct contact with the wearer-facing surface of the inner sheet such that the hooks are configured to engage the wearer-facing surface of the inner sheet, wherein the plurality of hooks are created from the backsheet.

2. The absorbent article of claim 1, wherein the plurality of hooks are configured to refastenably engage the wearer-facing surface of the inner sheet.

3. The absorbent article of claim 1, wherein the fastening component is positioned adjacent to the proximal edge of at least one of the first belt and the second belt.

4. The absorbent article of claim 1, wherein the laterally opposing side edges of the second belt are refastenably connected with laterally opposing side edges of the first belt.

5. The absorbent article of claim 1, wherein the absorbent article comprises a first waist region, a second waist region, and a crotch region positioned intermediate the first waist region and the second waist region, wherein the fastening component is positioned in the second waist region.

6. The absorbent article of claim 1, wherein the fastening component has a transverse width (WH) of from about 20 mm to about 120 mm.

7. The absorbent article of claim 1, wherein the fastening component has a longitudinal length (LH) of from about 5 mm to about 50 mm.

8. An absorbent article comprising:

a chassis comprising a topsheet, a backsheet, and an absorbent core positioned between the topsheet and the backsheet, the chassis further comprising a first end region and a second end region longitudinally separated from the first end region by a crotch region;

a first belt connected with the first end region of the chassis;

a second belt connected with the second end region of the chassis, wherein laterally opposing side edges of the second belt are connected with laterally opposing side edges of the first belt to form a waist opening and two leg openings;

wherein at least one of the first belt and the second belt comprises:

a distal edge extending along a portion of the waist opening;

a proximal edge extending along a portion of each of the leg openings;

an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet; and a fastening component comprising a plurality of hooks, wherein the fastening component is positioned adjacent to the proximal edge of at least one of the first belt and the second belt, and wherein the hooks are covered by the wearer-facing surface of the inner sheet, wherein the plurality of hooks are integrally formed from the backsheet.

9. The absorbent article of claim 8, wherein the backsheet is a laminate comprising a film and a nonwoven.

10. The absorbent article of claim 9, wherein the fastening component is bonded with the film.

11. The absorbent article of claim 9, wherein the fastening component is bonded to the nonwoven.

12. The absorbent article of claim 9, wherein the fastening component is partially bonded to the film and partially bonded to the nonwoven.

13. The absorbent article of claim 8, wherein at least one of the first belt, second belt, or backsheet comprises one or more design elements adapted to indicate the location or function of the fastening component, the one or more design elements comprising at least one of insignia, letters, words, graphics, logos, colors, fonts, shapes, or combinations thereof.

14. The absorbent article of claim 8, wherein the absorbent article comprises a garment-facing surface and a wearer-facing surface, wherein the fastening component is visible from the garment-facing surface.

15. An absorbent article comprising:

a chassis comprising a topsheet, a backsheet, and an absorbent core positioned between the topsheet and the backsheet, the chassis further comprising a first end region and a second end region longitudinally separated from the first end region by a crotch region;

a first belt connected with the first end region of the chassis;

a second belt connected with the second end region of the chassis, wherein laterally opposing side edges of the second belt are connected with laterally opposing side edges of the first belt to form a waist opening and two leg openings;

wherein at least one of the first belt and the second belt comprises:

a distal edge extending along a portion of the waist opening;

a proximal edge extending along a portion of each of the leg openings;

an inner sheet and an outer sheet, wherein the inner sheet and the outer sheet each comprise a wearer-facing surface and a garment-facing surface; and an elastic material positioned between and connected with the garment-facing surface of the inner sheet and the wearer-facing surface of the outer sheet; and two or more fastening components, each fastening component comprising a base comprising a first surface; a second surface opposite the first surface, and a plurality of hooks extending from the second surface, wherein the first surface of the base is bonded with the backsheet and wherein each of the fastening components are covered by the wearer-facing surface of the inner sheet, wherein the plurality of hooks are in direct contact with the wearer-facing surface of the inner sheet.

16. The absorbent article of claim 1, wherein the fastening component is positioned from about 2 mm to about 15 mm from the proximal edge of the first belt or the second belt.

17. The absorbent article of claim 1, wherein the hooks comprise a basis weight of from about 40 gsm to about 150 gsm and a height of from about 120 μm to about 520 μm.

18. The absorbent article of claim 1, wherein the fastening component comprises a color.

19. The absorbent article of claim 1, wherein the backsheet comprises a nonwoven.

20. The absorbent article of claim 1, wherein the plurality of hooks comprise at least one of a nub shape, a mushroom shape, a "J" shape, a "T" shape, or a hook shape.

* * * * *